United States Patent
Wilkinson et al.

(10) Patent No.: US 10,036,730 B2
(45) Date of Patent: Jul. 31, 2018

(54) ARRAY OF RESONANT SENSORS UTILIZING POROUS RECEPTOR MATERIALS WITH VARYING PORE SIZES

(71) Applicant: MATRIX SENSORS, INC., San Diego, CA (US)

(72) Inventors: Paul R Wilkinson, El Segundo, CA (US); Steven Yamamoto, San Diego, CA (US)

(73) Assignee: MATRIX SENSORS, INC., San Diego, CA (US)

( * ) Notice: Subject to any disclaimer, the term of this patent is extended or adjusted under 35 U.S.C. 154(b) by 730 days.

(21) Appl. No.: 14/592,896

(22) Filed: Jan. 8, 2015

(65) Prior Publication Data

US 2015/0192548 A1 Jul. 9, 2015

Related U.S. Application Data

(60) Provisional application No. 61/925,643, filed on Jan. 9, 2014.

(51) Int. Cl.
  *G01N 29/036* (2006.01)
  *G01N 29/02* (2006.01)
  *G01N 29/24* (2006.01)

(52) U.S. Cl.
  CPC ......... *G01N 29/036* (2013.01); *G01N 29/022* (2013.01); *G01N 29/2406* (2013.01); *G01N 29/2437* (2013.01); *G01N 2291/0256* (2013.01); *G01N 2291/0427* (2013.01); *G01N 2291/106* (2013.01)

(58) Field of Classification Search
  CPC ............... G01N 29/036; G01N 29/022; G01N 29/2406; G01N 29/2437; G01N 2291/0256
  USPC .......................................................... 73/579
  See application file for complete search history.

(56) References Cited

U.S. PATENT DOCUMENTS

| | | | |
|---|---|---|---|
| 7,305,883 B2 * | 12/2007 | Khuri-Yakub | G01N 27/221 73/579 |
| 8,065,904 B1 | 11/2011 | Allendorf | |
| 8,424,370 B2 | 4/2013 | Cable | |
| 8,480,955 B2 | 7/2013 | Yaghi | |
| 8,542,023 B2 | 9/2013 | Potyrailo | |
| 8,542,024 B2 | 9/2013 | Potyrailo | |
| 8,718,956 B2 | 5/2014 | Hesketh | |
| 8,735,161 B2 | 5/2014 | Yaghi | |
| 2010/0180673 A1 * | 7/2010 | Cable | G01N 29/036 73/64.53 |
| 2012/0282142 A1 | 8/2012 | Fleischer | |
| 2014/0106468 A1 | 4/2014 | Boersma | |

* cited by examiner

*Primary Examiner* — Son Le
*Assistant Examiner* — Tarun Sinha
(74) *Attorney, Agent, or Firm* — Mark B. Floyd (57) ABSTRACT

A sensor array comprises resonant sensors and porous receptor materials arranged on the resonant sensors to absorb or adsorb one or more analytes. The average pore size of the porous receptor materials on the sensors increases systematically from one sensor to the next in the array. At least one detector is arranged to detect responses of the resonant sensors when the array is exposed to a sample potentially containing one or more of the analytes. In some embodiments, a processor is programmed to determine from the sensor responses the presence, amount or relative concentration of target molecules in the sample.

31 Claims, 5 Drawing Sheets

ARRAY OF RESONANT SENSORS UTILIZING POROUS RECEPTOR MATERIALS WITH VARYING PORE SIZES

CROSS REFERENCE TO RELATED APPLICATIONS

This application claims the benefit of U.S. provisional patent application 61/925,643 filed on Jan. 9, 2014, which application is hereby incorporated by reference in its entirety.

BACKGROUND

The invention relates to sensor arrays for detecting substances, and in particular to an array of resonant sensors utilizing porous materials with varying pore sizes as receptors.

Resonant sensors use target molecules adsorbed in the sensing material to change properties that are reflected in the resonance frequency. A wide variety of cantilever, membrane and piezoelectric resonator-based sensors have been fabricated using MEMS technology. These sensors generally detect agents through the use of polymer films and coatings with selective adsorption for a specific agent or set of agents. Although these sensors provide a certain degree of sensitivity, it is desirable in many applications to have sensors with even higher sensitivities.

A capacitive micromachined ultrasonic transducer (cMUT) is a micromachined device having a substrate and a membrane supported above the substrate by an insulating material. A variable voltage applied between the substrate and membrane drives the membrane to vibrate and emit sound waves at ultrasonic frequencies. Arrays of cMUTs have been used for transmitting and receiving ultrasonic beam patterns in air and water over a frequency range from 10 kHz to 100 MHz. These cMUTs rely on the large electric field ($E>10^8$ V/m) in the gap of the capacitor to provide an electromechanical coupling coefficient close to unity.

cMUTs are mostly used for medical imaging. In addition, they have been used to indirectly measure various fluid characteristics, based on processing of ultrasonic signals transmitted and received through the fluid. In current cMUT devices and applications, the cMUT elements are used to transmit and/or receive ultrasonic energy between the cMUT element and the environment. Moreover, to ensure reliable and consistent operation, cMUT element membranes are normally designed to be non-reactive to chemicals, light, and other environmental factors that may alter or interfere with their operational characteristics. However, due to their resonant character, cMUT devices have the potential to be used as sensors, in a manner similar to MEMS cantilever, membrane, and piezoelectric resonator-based sensors.

U.S. Pat. No. 7,305,883 to Khuri-Yakub discloses arrays of sensors. Sensor elements include a functionalized membrane supported over a substrate by a support frame. The sensor element is connected to an electrical circuit, which is configured to operate the sensor element at or near an open circuit resonance condition. The mechanical resonance frequency of the functionalized membrane is responsive to binding of an agent to the membrane. The exterior surface of each sensor membrane is chemically functionalized to have an affinity for one or more specific, predetermined chemicals. A detector provides a sensor output responsive to the mechanical resonance frequency of the sensor element.

US patent application 2010/0180673 discloses a method for analyzing liquid samples by applying a liquid to a cMUT device having an array of sensors, drying the sensors, and electronically detecting an agent bound to each of the plurality of sensors. An electrical circuit provides a sensor output responsive to a mechanical resonance frequency of the sensor. The exterior surface of sensor membrane is chemically functionalized to have an affinity for one or more specific, predetermined chemicals. The mechanical resonance frequency of the sensor is responsive to the binding of an agent to the functionalized membrane, and the mass of the agent bound to each of the sensors may be determined.

SUMMARY

According to one aspect, a device comprises a sensor array having at least three resonant sensors and porous receptor materials arranged on the resonant sensors to absorb or adsorb one or more analytes. The average pore size of the porous receptor materials on the sensors increases systematically from the porous material on a first one of the sensors, to the porous material on a second one of the sensors, and to the porous material on a third one of the sensors. At least one detector is arranged to detect responses of the resonant sensors when the array is exposed to a sample potentially containing one or more of the analytes.

According to another aspect, a method comprises exposing a sensor array to a sample that potentially contains one or more analytes. The sensor array includes at least three resonant sensors and porous receptor materials arranged on the resonant sensors to absorb or adsorb the one or more analytes. The average pore size of the porous receptor materials on the sensors increases systematically from the porous material on a first one of the sensors, to the porous material on a second one of the sensors, and to the porous material on a third one of the sensors. Responses of the sensors to the sample are detected, and at least one processor is employed to determine from the sensor responses if the sample contains one or more of the analytes.

According to another aspect, a device comprises a sensor array having a plurality of resonant sensors and porous receptor materials arranged on the resonant sensors. The average pore size of the porous receptor materials on the sensors increases from the average pore size of a first one of the porous materials on a first one of the sensors to the average pore size of a second one of the porous materials on at least a second one of the sensors. At least one detector is arranged to detect responses of the sensors when the sensor array is exposed to a sample. At least one processor is in communication with the detector for receiving signals or data representative of the sensor responses. The processor is programmed to determine from the sensor responses the presence, amount or relative concentration of target molecules having a size larger than the average pore size of the first one of the porous materials on the first sensor and smaller than the average pore size of the second porous material on the second sensor.

According to another aspect, a method comprises exposing a sensor array to a sample that potentially contains one or more target molecules. The sensor array comprises a plurality of resonant sensors and porous receptor materials arranged on the resonant sensors. The average pore size of the porous receptor materials on the sensors increases from the average pore size of a first one of the porous materials on a first one of the sensors to the average pore size of a second one of the porous materials on at least a second one of the sensors. Responses of the sensors to the sample are detected, and at least one processor is employed to determine from the sensor responses the presence, amount or relative concentration of the target molecules having a size larger than the average pore size of the first one of the porous materials on the first sensor and smaller than the average pore size of the second porous material on the second sensor.

BRIEF DESCRIPTION OF THE DRAWINGS

The foregoing aspects and advantages of the present invention will become better understood upon reading the following detailed description and upon reference to the drawings where.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. a signal or data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass non-transitory media such as magnetic, optic, and semiconductor storage media (e.g. hard drives, optical disks, flash memory, DRAM), as well as communications links such as conductive cables and fiber optic links. According to some embodiments, the present invention provides, inter alia, computer systems comprising hardware (e.g. one or more processors and associated memory) programmed to perform the methods described herein, as well as computer-readable media encoding instructions to perform the methods described herein.

The following description illustrates embodiments of the invention by way of example and not necessarily by way of limitation.

Figure 1:
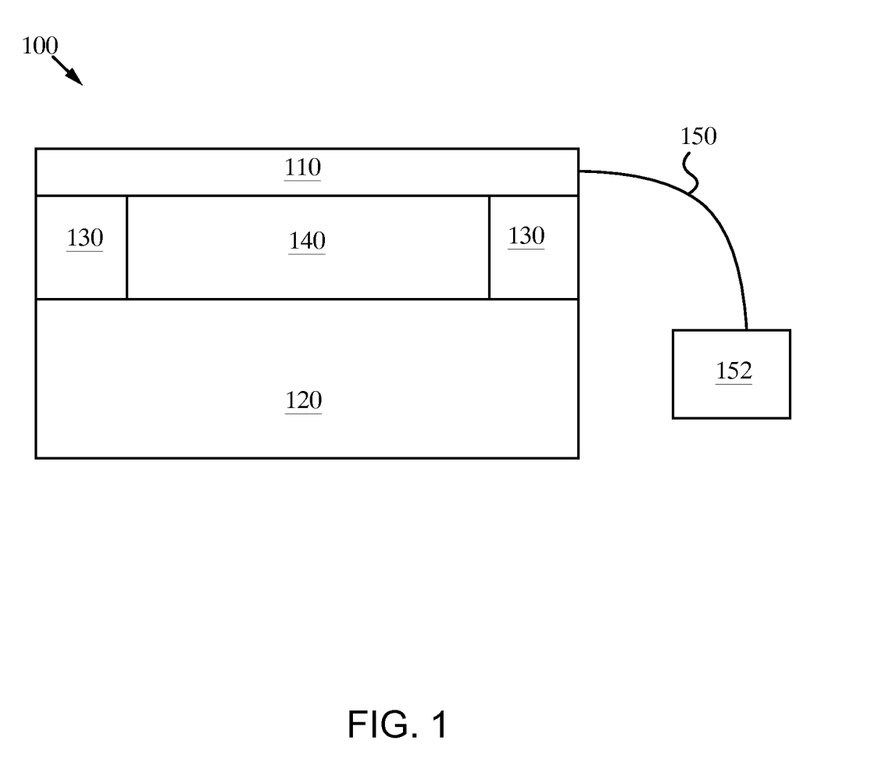
FIG. 1 shows a schematic, cross-sectional view of a sensor according to one embodiment of the invention.
Figure 2:
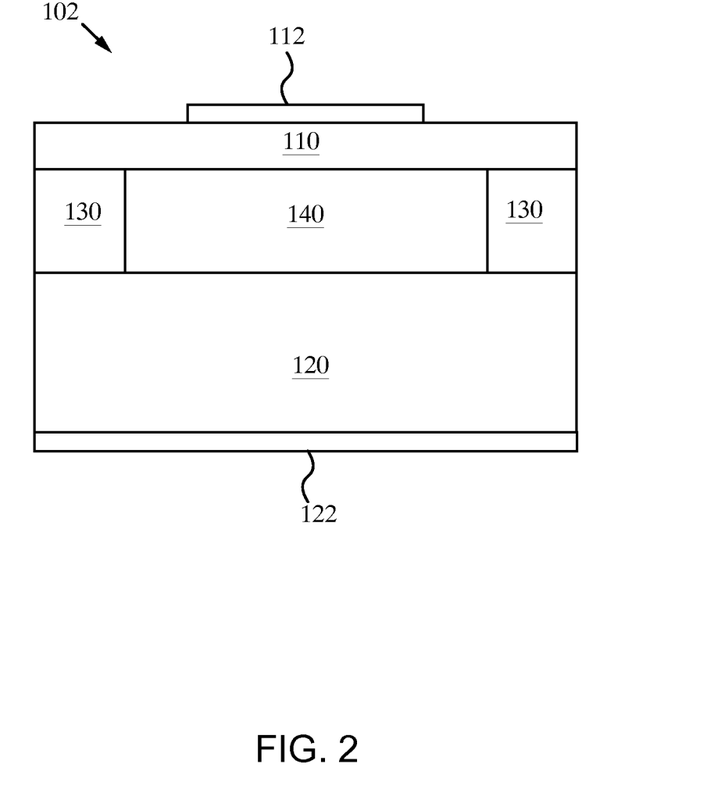
FIG. 2 shows a schematic cross-sectional view, of a sensor according to another embodiment of the invention.

FIGS. 1 and 2 shows schematic cross-sectional diagrams of two examples of resonant sensors according to some embodiments of the invention. Resonant sensors include, without limitation, capacitive micromachined ultrasonic transducer (cMUT), cantilever, quartz crystal microbalances, and piezoelectric resonant-based sensors. FIG. 1 shows a cMUT sensor 100 that has a membrane 110 which is functionalized with a metal-organic framework (MOF) for adsorbing or binding one or more substances (e.g., target molecules of interest). The membrane 110 is supported over a substrate 120 by support frame 130. The membrane 110, support frame 130 and substrate 120 define a vacuum gap 140. Vacuum gap 140 is preferably between about 0.1 µm and about 0.5 µm in height.

The sensor 100 is connected to a detector 152 through a connector 150. In general, the detector 152 preferably employs a detection modality to measure a sensor response (e.g., a change in the position or resonance frequency of the resonating element, such as the membrane 110) due to the mass of one or more analytes adsorbed or bound to the sensor 100. In preferred embodiments, the detector 152 detects a resonance frequency of the functionalized membrane 110, which frequency may change due to the mass of one or more substances adsorbed or bound to the MOF on the membrane 110. Suitable detectors include, but are not limited to, an optical detector, a mechanical stress detector, a magnetic detector, and a capacitance detector.

In one embodiment, the membrane 110 is driven thermally (by applied heat or by thermal noise) or electrically, and an optical detector is used to detect deflection or resonant frequency shifts of the membrane 110. Interferometric optical detection techniques are described in U.S. Pat. No. 6,567,572, by Degertekin et al., which is incorporated herein by reference. In other embodiments, the membrane 110 has thin piezoelectric or magnetic films that provide coupling. The resonant membranes 110 may be addressed by capacitor action (cMUTs), by a piezoelectric thin film (pMUTs), or by a magnetic film on the surface (mMUTs). Alternatively, a change in membrane deformation may be detected directly through a change in capacitance, or magnetic field, or piezoelectric signal, or change in resistance through the piezoresistive effect, or optically using an interferometer, or any other detection modality to measure the response of sensor 100 due to the mass of one or more substances adsorbed or bound thereto, or due to a stiffening effect when one or more analytes is adsorbed or absorbed. Preferably, the membrane 110 operates at a mechanical resonance frequency of at least about 1 MHz, more preferably between about 1 MHz and about 100 MHz.

FIG. 2 shows a cMUT sensor 102 having a membrane 110 that includes a first electrode 112. The substrate 120 contains a second electrode 122. The membrane 110 and the substrate 120 are preferably thin membranes that are essentially parallel plate capacitors with a gap between the plates. In a preferred aspect of this embodiment, the conductive silicon wafer on which the membrane is fabricated, i.e. substrate 120, makes up one plate of the capacitor. A metal electrode 112 on top of the membrane 110 is the other plate of the capacitor. The membrane 110, which is supported by insulating support frame 130, is typically made of an insulating material, most commonly silicon, and is coated with the electrode 112. A low temperature oxide passivation layer may cover the electrode 112 and the membrane 110.

Figure 3:
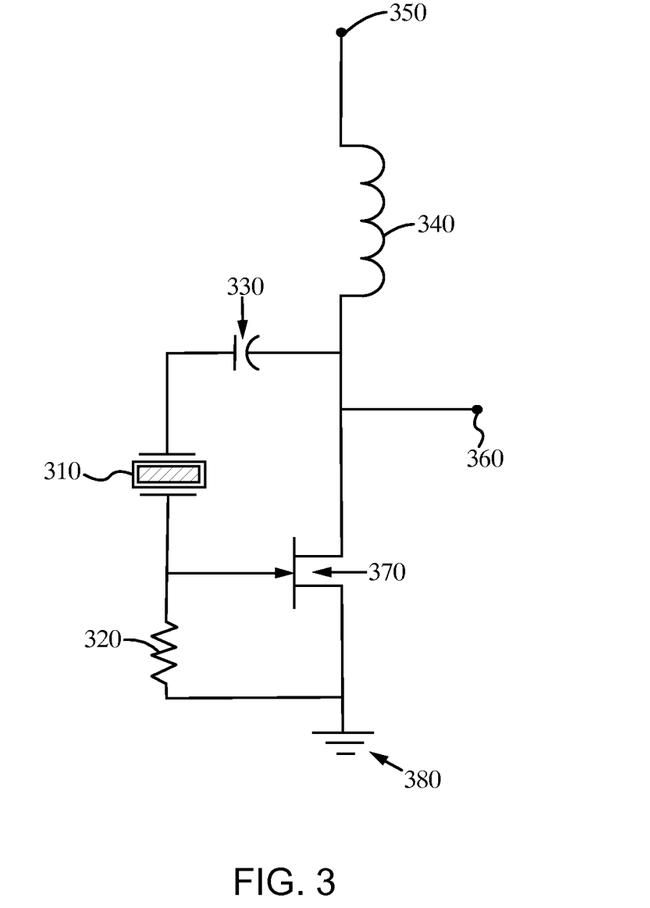
FIG. 3 shows an example of an electrical circuit for a sensor according to some embodiments of the invention.

FIG. 3 shows one embodiment of a circuit that is suitable for use with a resonant sensor. The circuit is one variation of an oscillator. The circuit includes a resonant sensor 310, resistor 320, capacitor 330, inductor 340, DC voltage source 350, sensor output 360, transistor 370, and connection to ground 380. Many other circuits are available to establish a resonant circuit using the sensor's resonant electrical input impedance (e.g., a Colpitts oscillator, Pierce oscillator, etc.). The output of these circuits is an approximately sinusoidal signal whose frequency is the measurable quantity of interest.

In some embodiments, the sensor is placed in the feedback loop of an amplifier and the gain of the amplifier is adjusted such that the circuit oscillates. The frequency of the oscillator is tuned by adjusting the DC bias that is applied to the sensor element. By controlling this DC bias the resonance or oscillation frequency is placed near the open circuit resonant frequency of the sensor. This is done in order to reduce the noise in the oscillator circuit, and hence increase the sensitivity of the sensor. When analyte adsorbs or binds to the MOF on a resonating member of the sensor (e.g., the membrane 110 or a cantilever), its open circuit resonance frequency shifts, and this imparts a frequency shift in the oscillator circuit. By measuring the resonance frequency of the oscillator, one can tell how much mass has deposited on the membrane 110 functionalized with a MOF.

Figure 4:
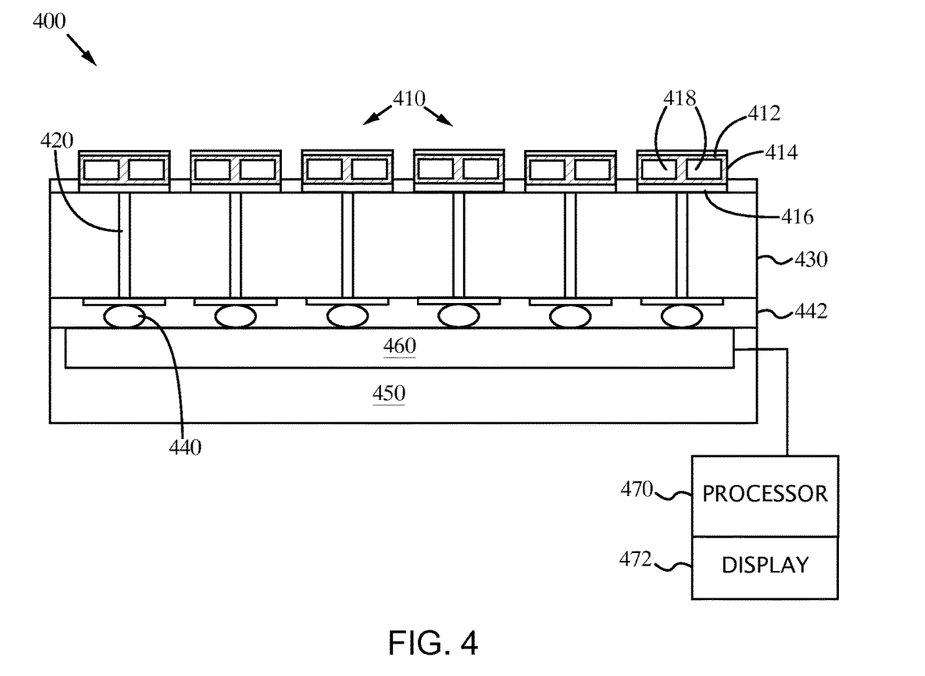
FIG. 4 shows a schematic, cross-sectional view of an array of sensors according to some embodiments of the invention.

FIG. 4 is a schematic cross-sectional view of a sensor device 400 having an array of sensors 410 according to an embodiment of the invention. In this example, each sensor 410 contains two sensor elements, each of which has a membrane 412, support frame 414, substrate 416 and vacuum gap 418. The exterior surface of each membrane 412 is functionalized with a porous receptor material, such as a MOF. The sensors are designed for sensitivity to mass loading and stress loading by substances adsorbed or bound to the membrane 412, and for matching into the electronic circuitry such as a Pierce oscillator or any other type of oscillator that is used to detect the shift in the property of the membrane 412. The porous receptor material (e.g., MOF) on the resonating element (e.g., the membrane 412) adsorbs or absorbs molecules when they are present in a sample (e.g., ambient or environmental air) to which the sensor is exposed. Consequently, the operational characteristics (e.g., impedance or resonance frequency) of the sensor will be altered, and this sensor response is detected.

The presence or amount of substance(s) in a sample is measured by detecting the alteration of the operating characteristics of the resonating element (e.g., a membrane or cantilever). For example, an alteration in sensor characteristics can be detected by measuring the impedance of the sensor, or by measuring the change in the resonant frequency of the functionalized membrane 412. Interconnects 420 through a first wafer 430 provide electrical contacts from the sensors 410 to a second wafer 450 with an electronics layer 460. The interconnects 420 are separated from the electronics layer 460 by an underfill 442 and solder balls 440. (While solder bumps are shown in this figure, contacts may be made between the first wafer 430 and the second wafer 450 by any means known in the art, e.g. with an anisotropic conducting film).

The electronics layer 460 contains appropriate circuitry to drive and detect operational characteristics of the sensors 410, such as resonance frequencies of each membrane 412. Additional signal processing electronics or a processor 470 may be attached to the sensor electronics to further process the signals or data and to indicate the presence and/or amount of substance(s) in a sample. For example, the relative concentration of one or more analytes may be shown via the display 472 in communication (wirelessly or with wires) with the processor 470. The processor 470 receives signals or data representative of the resonance frequencies (e.g., frequency output signals from the sensors 410) to determine the presence or amount of analyte(s). The processor 470 may be a microprocessor included with the device 400. Alternatively, processing functions may be performed in a separate processor or external computer in communication with the electronics layer 460. The external processor or computer receives data representative of the measured resonance frequencies and determines the presence or amount of analyte(s). Alternatively, multiple processors may be provided, e.g., providing one or more processors in the device 400 that communicate (wirelessly or with wires) with one or more external processors or computers.

Some processing of data can be done near the sensor. For instance, time averaging or multiplexing or digitization can be all processed in the vicinity of the sensor before being transmitted to a computer or a circuit board with a multi-processor. Specific algorithms can be loaded in memory to perform the same functions one would in a digital computer and then drive displays where colored outputs can be used to indicate level of detection or hazard. As in many sensors deployed today, such as RF tags and implanted medical devices, it is possible to use RF antennas to couple and provide power to the sensor. Once a sensor is powered, it senses its function, and then the output of the sensor is re-radiated to a receiving antenna. In this fashion, the sensor device 400 can be passive and remotely addressed.

In some embodiments, a CMOS provides the circuitry to detect the mass loading of the membrane 412 either through an impedance change, by direct measurement, resonance frequency measurement, or any of various other means. The outputs of various sensors can be multiplexed, then a frequency counter can measure the frequencies. These outputs can then be digitized and stored and processed in a processor. The processor then can display the variation of the resonant frequency versus time and provide results of analysis of sensed species based, for example, on previously loaded models of sensitivity of multiple sensors to various chemicals.

The material properties and dimensions of the membranes 412 contribute to their resonant frequencies. In some embodiments, a DC bias is applied to the membranes 412 to maintain a very high electric field in the vacuum gaps 418. For instance, a silicon membrane 12 μm in diameter and 0.4 μm thick may resonate at a frequency of 42 MHz. In some embodiments, each sensor is used as the resonant tank of an oscillator circuit, where the resonant frequency shift indicates the amount of mass loading on the membranes 412. The sensitivity of such a resonator is defined as the ratio of the frequency shift over the frequency: $\Delta f/f = -\Delta m/2\, m$, where $\Delta m$ is the change in mass (i.e., mass of the species that adsorbs or binds to the sensor) over the total mass of the membrane. In some embodiments, a resonance frequency response of the fundamental mode is supplemented by also measuring a series of higher harmonics of the membrane.

In another embodiment, gases or liquids are exposed over a layer of porous receptor material that adsorbs or absorbs the one or more analytes (e.g., molecules of interest). The temperature of exposure will depend on the chemical desorption rate, and may be at room temperature or at lower temperatures depending on the molecule. After a set time, the sensor elements 410 may be heated either by thermal pulse or a linear programmed temperature ramp. During this heating, the molecules are desorbed and the change in resonant frequency and Q-factor shows a particular desorption profile similar to thermal desorption analysis commonly using spectrometric systems or gravimetrically (thermogravimetry). The temperature of desorption is an additional parameter that is sensitive to the chemical nature of the absorbent-absorbate interaction. After one thermal desorption cycle, a second subsequent cycle may be used to provide a reference calibration to be subtracted as a baseline from the first. The second thermal cycle reflects the thermomechanically induced change in resonance frequency.

Referring again to FIG. 2, the use of electrodes 112 provides a convenient method to heat the membrane 110. The small size and structure of the sensors ensures that low energy consumption, low thermal loads and fast (sub millisecond) response times can be achieved. The rapid response times aid resolution in the desorption profile. Temperature readouts of the sensors are also possible through integration of small thermocouples or the resistance of piezoresistive layers. In other embodiments, one or more heaters may be used to heat the sensors with MOFs. This may be especially useful in applications where the adsorption or binding is not reversible at room temperature, since heat provides energy for desorption and tends to reset the sensors. There are indications that water binds irreversibly to MOFs, so heating can be useful. Also, the adsorbed species may be determined based on the temperature at which desorption occurs. This may be most useful for sensors designed for irreversible binding (e.g., the sensors collect molecules for a period of time, and then the adsorbed mass is tracked as the molecules are removed from the MOFs thermally).

Sensor arrays may be configured as one-dimensional arrays of sensors or two-dimensional arrays of sensors. An advantage of a two-dimensional array is that an entire wafer may be populated with thousands of sensors. A one-dimensional array provides surface space, which may be used to integrate electronics side-by-side with the sensors. In some embodiments, a two-dimensional sensor array has electronics flip-chip bonded or fabricated under the sensor array. A sensor array with thousands of membranes may be useful in some embodiments for establishing the electrical impedance of the sensor, or for reducing the number of false alarms, if all the membranes in a sensor array are arranged to operate in parallel. If one sensor were to give a false indication, then the other sensors force a correct decision. Having thousands of sensors, many of which are functionalized in the same fashion, can also be used to reduce the false alarm rates and provide a more stable measurement of the presence of one or more analytes.

Suitable porous receptor materials include porous crystalline materials such as a metal-organic frameworks (MOFs), porous coordination polymer, or porous coordination frameworks. Preferred MOF subclasses include Zeolitic imidazolate framework (ZIF), IRMOF, and Multivariate MOF (MTV-MOF) made using a mix of organic linkers having the same geometry but varied chemical functionality. Suitable porous receptor materials also include a covalent organic framework (COF) in which the framework includes covalent chemical bonds rather than metal coordination bonds, and Zeolite which is a class of inorganic porous crystalline materials. In rare embodiments, the porous receptor materials comprise non-crystalline porous materials such as Metal-organic Polyhedron having discreet porous cages, Porous metal-organic polymer, Metal-organic gel, or Porous Carbon (also known as activated carbon).

Metal-organic frameworks (MOFs) are an expanding class of porous crystalline materials that are built up from nodes of metal ions connected by organic linkers. These materials can typically be engineered to have pore apertures with a width or diameter in a range of less than 1 Angstrom to about 30 Angstroms (Yaghi, et. al., Nature 423, 705-714, Jun. 12, 2003). A class of exotic MOFs ("MOF-74") with pore aperture diameters of 98 Angstroms have also been demonstrated (Deng, et. al., Science 336, 1018, 2012). MOFs with varying pore sizes can selectively adsorb molecules based on the size of the molecules. For example, engineered MOFs with pore sizes designed for carbon dioxide ($CO_2$) adsorption can separate gases in industrial processes (Du, et. al., J. Am. Chem. Soc., 2013, 135 (2), pp 562-565). MOFs can also be used as receptor layers with a Quartz Crystal Microbalance (QCM) to act as a chemical sensor in controlled environments.

The pore size of the MOF (e.g., the average width, diameter or volume of the pore apertures) is preferably chosen to achieve a degree of selectivity of adsorbed molecules based on the size of the molecules. In some embodiments, an array of resonant sensors has MOFs of varying pore size on the resonating elements of the sensors to provide a new type of "size spectrometer". This "size spectrometer" could also be used as a chemical sensor where ambient molecular concentrations are monitored in real-time and the multiple sensors with varied pore sizes provide selectivity based on molecule size.

Figure 5:
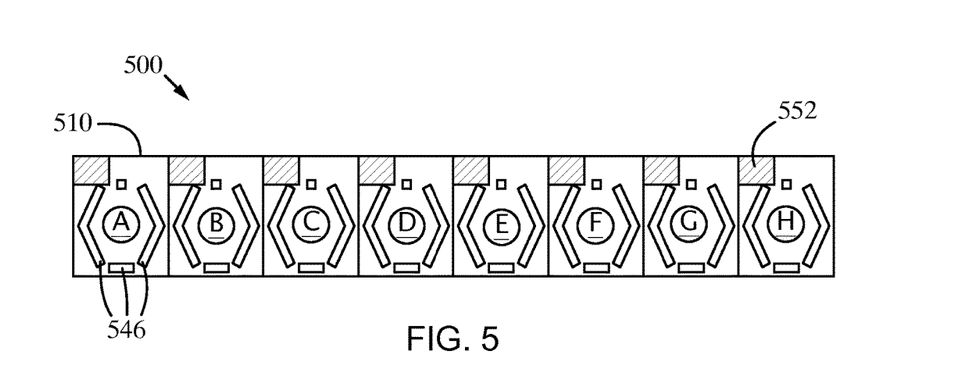
FIG. 5 shows a schematic, plan view of an array of sensors according to some embodiments of the invention.

FIG. 5 shows a sensor array 500 that includes eight resonant sensors 510. Each of the resonant sensors has a respective resonating element, and eight MOFs A-H are disposed on the resonating elements. The average pore size of the MOFs increases systematically from the MOF A on the first sensor to the MOF H on the eighth sensor (i.e., the pore size of MOF A<B<C<D<E<F<G<H). To mechanically isolate each of the sensors 510 and/or to reduce crosstalk between the sensors, vertical trenches 546 may be added between each of the sensors. The trenches 546 may be formed by any known etching process. Each of the sensors 510 may also include wire bond pad areas 552 for electrical connections.

Each of the sensors 510 has a respective resonating element that is coated with a MOF having a different average pore size. The response of each sensor 510 (e.g., its change in resonance frequency) provides an output signal indicative of the mass of all molecules that are small enough to fit inside the pores of that particular MOF. By taking the difference of mass signals between two MOFs having different average pore sizes (pore size MOF A<B), we get a signal that is proportional to the mass of all molecules having a size larger than the pore size of MOF A and smaller than the pore size of MOF B. In some embodiments, we extend this concept to more sensors coated with MOFs having different average pore sizes to create a "size spectrometer" based on molecular size.

Figure 6:
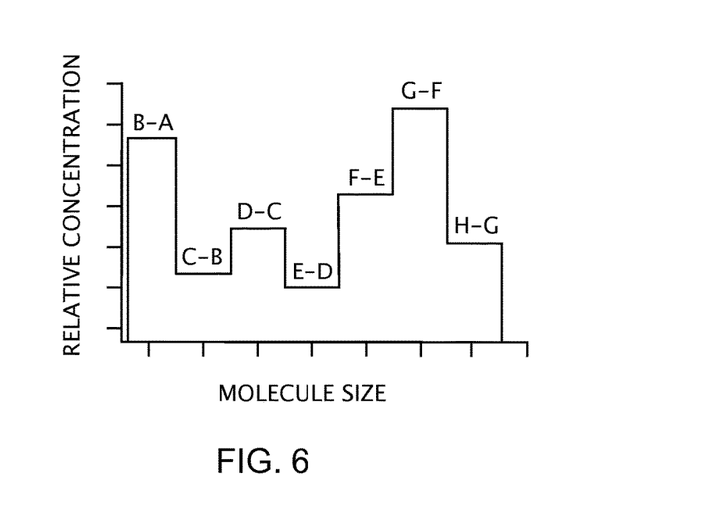
FIG. 6 is a graph showing relative concentration of different molecule sizes according to some embodiments of the invention.

FIG. 6 is a graph illustrating what such a size spectrograph might look like for an 8-sensor array that provides (N−1) differences in the average pore sizes of the MOFs from one sensor to the next in the array, where N is the number of sensors coated with a MOF in the array. In the graph, the bar B-A indicates the relative concentration of molecules having a size larger than the pore size of MOF A and smaller than pore size of MOF B, the bar C-B indicates the relative concentration of molecules having a size larger than the pore size of MOF B and smaller than the pore size of MOF C, the bar D-C indicates the relative concentration of molecules having a size larger than the pore size of MOF C and smaller than the pore size of MOF D, the bar E-D indicates the relative concentration of molecules having a size larger than the pore size of MOF D and smaller than the pore size of MOF E, the bar F-E indicates the relative concentration of molecules having a size larger than the pore size of MOF E and smaller than the pore size of MOF F, the bar G-F indicates the relative concentration of the molecules having a size larger than the pore size of MOF F and smaller than the pore size of MOF G, and the bar H-G indicates the relative concentration of the molecules having a size larger than the pore size of MOF G and smaller than the pore size of MOF H.

In some embodiments, the average pore size of the MOFs A-H on the resonant sensors 510 increases or decreases mathematically (e.g., either linearly changing average pore sizes in set increments from one sensor to the next in the sensor array 500 or logarithmically changing the average pore sizes of the MOFs on the sensors 510). In preferred embodiments, the average pore sizes of the porous receptor materials A-H are determined by a combination of factors including: the number of sensors 510 in the array 500, the sizes and types of molecules to be detected for an intended application (e.g., a sensor array for use in an oil well is exposed to different molecules than a sensor array used in an office building), and the ability to synthesize and deposit a robust film of a given pore size on the resonating elements of the sensors 510. Consequently, the pore sizes are not limited to varying in a mathematically simple fashion (e.g., linear, logarithmic, etc.). It's also possible to choose the average pore sizes based on the size distribution of the target molecules in an intended application. In preferred embodiments, optimal pore sizes are selected to minimize the number of sensors 510 that are needed to detect the analytes, typically target molecule(s), in a given application, or to maximize selectivity of the target molecule(s) based on the differences in average pore sizes of the porous receptor materials. For many uses (e.g., as a room-temperature gas sensor), each of the porous receptor materials has pore apertures having an average width or diameter in the range of 1 to 30 Angstroms to adsorb similarly sized molecules.

MOFs A-H may be placed on the resonating elements of the sensors 510 using various techniques such as ink jetting and electrospray. Other techniques for area-selective deposition of MOF materials on the resonating elements of the sensors 510 include, by way of example but not limitation: pre-patterning self-assembled monolayers (SAMs) that behave as presenting-ligands for subsequent MOF growth; metal films that are used as metal ions source for MOF growth; seeds to promote MOF nucleation; and/or droplets of mother solution to confine MOF synthesis. MOFs may also be positioned on the sensors by fabrication of microstructures in a pre-prepared MOF thin film using photolithography. Other techniques include, layer-by-layer growth to thicken MOF films, producing MOF heterostructures, and the fabrication of MOF/metal hybrid multilayer structures.

At least one processor may be employed to determine the presence and/or amount (e.g., quantity, mass or relative concentration) of one or more substances (e.g., molecules of interest such as target analytes). The processor receives signals or data representative of the sensor responses (e.g., changes in resonance frequencies of the functionalized sensors due to mass loading of molecules on the MOFs). In some embodiments, the processor deconvolves or de-convolutes the data using coefficients relating the sensor responses to the respective masses of the substances adsorbed or absorbed to the MOFs on the sensors. This step can be performed with a set of equations, or more generally by a matrix.

In a simple form, let A be the signal amplitude of sensor 1 indicating the sensor response to substances in a sample, and X the quantity of unknown target substance adsorbed on the sensor 1. We can describe the dependence of amplitude A and unknown quantity X by a linear relationship and a coefficient $a_x$ so that $A=a_x X$. If there is more than one substance on sensor 1, such as substances X and Y, then $A=a_x X+a_y Y$. If we now let B be the signal amplitude of the second sensor 2 with a MOF having a different average pore size and coefficients $b_x$ and $b_y$, and assume that the second sensor is exposed to the same quantities X and Y of substances (since the sensors are proximate), then we can measure a signal amplitude value B of the second sensor and solve two equations with two variables:

$$A=a_x X+a_y Y \quad (1)$$

$$B=b_x X+b_y Y \quad (2)$$

More generally, if we know the matrix of coefficients $a_{ij}$, then we can determine the masses of multiple substances $X_j$ if we have measured the amplitudes of I sensors $A_i$ using the vector product (equation 3):

$$A_i=a_{ij} \cdot X_j \quad (3)$$

If the number of sensors is greater than or equal to the number of target substances, the equation can be solved. For example, for a thirty-two sensor array, up to thirty-two different target molecules can be determined. In practice, however, one may choose some redundancy to improve accuracy. For example, one may choose to employ thirty-two sensors to target a more limited set of eight analytes.

An array of sensors is preferably calibrated to determine the values of the matrix $a_{ij}$, with known substances of interest $X_j$. The calibration data is stored either in a processor in the sensor array device or in a processor separate from the sensor array. In either case, the signals or data representative of the sensor responses may be deconvolved and analyzed to determine values representative of the quantity, mass or relative concentration of each substance of interest. The sensor response data may be used with calibration curves to quantify the amounts of one or more analytes (e.g., the ppm concentration of a specific gas). The presence and/or amounts of the substances of interest may be recorded in memory and/or displayed.

In some embodiments, a look-up table or calibration curve is used to determine the quantity of each substance of interest, according to the signals or data indicating the sensor responses. The look-up table or calibration curve may be in a microprocessor included with the sensor array. In some embodiments, the microprocessor is programmed to store measured signal values and/or to calculate analyte quantities or concentrations. Alternatively, these functions may be performed in a separate processor or external computer in communication with the sensor array. Alternatively, multiple processors may be provided, e.g., providing one or more processors in the sensor array that communicate (wirelessly or with wires) with one or more processors or computers external to the array.

Sensor arrays may be made with any of various known fabrication techniques including: SOI bonding, sacrificial layer, surface or bulk micromachining, and silicon on insulator bonding. The sensor is preferably designed for maximum sensitivity while taking into consideration its mechanical loading and electrical interfacing into the integrated (or non-integrated) electronic circuitry. Sensors may be integrated with electronics in any of various known configurations including: flip-chip bonding, elements constructed on top of electronics, or vice versa. The sensors may be fabricated with through-wafer vias or trench isolated by etching through the backside using various well-known techniques for cMUT fabrication. Techniques suitable for fabricating such sensors are known in the art and are described, for example, in B. T. Khuri-Yakub and L. Levin, U.S. Pat. No. 5,828,394, which is incorporated herein by reference.

In operation, a sensor array can be mounted on a wall, ceiling or other portion of a fixed structure, incorporated into a hand-held device, or mounted on a moving vehicle, to name just a few methods of exposing the sensor array to a sample. Depending on the specific application, it may be used with or without active circulation of gas or liquid over the sensors to expose the sensor array to molecules in the environment. A general guideline for high sensitivity in detection of small quantities of materials is to position the sensor as close to a sampling inlet as possible.

It will be clear to one skilled in the art that the above embodiments may be altered in many ways without departing from the scope of the invention. Many different permutations or arrangements may be used to realize the device and method of the invention. For example, sensor arrays containing multiple sensors may have membranes with different resonant frequencies. A membrane operating at low frequency yields a sensor more sensitive to stress on the membrane, whereas a membrane operating at high frequency gives a sensor that is more sensitive to mass loading. Combining various operating frequencies in one sensor thus provides a sensor with a greater versatility.

In some embodiments, electronics are integrated with sensor arrays, where multiple sensors are attached in parallel, and sensors are operated at different frequencies so that one output line may be used. For this purpose, different sensors may be built and operated at different frequencies. For example, a row of sensors can be made to resonate from 45 MHz to 55 MHz in 0.1 MHz intervals. Principles of dense wavelength division multiplexing (DWDM) may be used in such devices. A sensor for a Dog Nose type sensor may be made of one of multiple capacitor membranes that are all attached in parallel by virtue of having a metal electrode that covers all the sensors partially or fully. By altering the diameter of resonating elements, it is possible to change the frequency of operation. Having sensors operating at multiple frequencies can have advantages in electronic integration in transmitting information at different frequencies on the same channel, and in separating the influence of stress and mass loading on the shift in resonant frequency of a resonator.

In some embodiments, sensor arrays have a vast number of independently addressed sensors in the array to provide a massive redundancy. For instance, in an array of 5000 sensors, one can have a redundancy factor of 100 using 50 MOFs and reference materials. This ensures that false alarms or defective elements in the arrays, which might miss the detection of analytes, are not an issue in device operation. The sensor array may optionally include at least one reference sensor that is not coated with a MOF or receptor material. The one or more reference sensors provide a reference signal. The number of sensors in the array that will be used as references may be determined experimentally. Typically, it is expected that 1% to 50% of the sensors in the array will not be coated with a porous receptor material (e.g., non-functionalized or passivated sensors) and be used as a reference. The self-calibration and learning feature of sensor arrays may take advantage of redundancy. New target substances may be quickly introduced into the detection capabilities of sensor array devices installed at different operating locations.

In some embodiments, multiple materials may be disposed on the array of resonant sensors including: MOFs with varying pore size, MOFS with varying chemical affinity to analytes, polymers, metals, etc. A porous receptor material is used as the sensing material either alone or in combination with inorganic materials, organic materials, conductive materials (e.g., inorganic conductors or organic conductors), polymers (e.g., conductive or non-conductive polymers). The porous materials (e.g., MOF material) of the disclosure can be combined with other materials for purposes of detecting target analyte(s).

Accordingly, the scope of the invention should be determined by the following claims and their legal equivalents.

What is claimed is:

1. A device comprising:
   a) a sensor array comprising at least three resonant sensors;
   b) porous receptor materials arranged on the resonant sensors to absorb or adsorb one or more analytes, wherein the average pore size of the porous receptor materials on the sensors increases systematically from the porous material on a first one of the sensors, to the porous material on a second one of the sensors, and to the porous material on a third one of the sensors; and
   c) at least one detector arranged to detect responses of the resonant sensors when the array is exposed to a sample potentially containing one or more of the analytes.

2. The device of claim 1, further comprising at least one processor in communication with the detector for receiving signals or data representative of the sensor responses, wherein the processor is programmed to determine the presence and/or amounts of the one or more analytes according to the sensor responses.

3. The device of claim 2, wherein the processor is programmed to determine respective amounts of the one or more analytes using coefficients relating the sensor responses to the respective masses of the analytes adsorbed or absorbed to the porous receptor materials.

4. The device of claim 1, wherein the porous receptor materials comprise metal-organic frameworks.

5. The device of claim 4, wherein each of the metal-organic frameworks has pore apertures having an average width or diameter in the range of 1 to 30 Angstroms.

6. The device of claim 1, wherein the sensor array includes at least four resonant sensors having respective resonating elements with porous receptor materials disposed thereon, and wherein the average pore size of the porous receptor materials increases systematically from the porous receptor material on the first sensor to the porous receptor material on the fourth sensor.

7. The device of claim 1, wherein the resonant sensors comprises capacitive micromachined ultrasound transducers having respective membranes, and wherein the porous receptor materials are positioned on the membranes.

8. The device of claim 1, wherein the sensor responses comprise frequency shifts.

9. A method comprising:
   a) exposing a sensor array to a sample or an environment that potentially contains one or more analytes, the sensor array including at least three resonant sensors and porous receptor materials arranged on the resonant sensors, wherein the average pore size of the porous receptor materials on the sensors increases systematically from the porous material on a first one of the sensors, to the porous material on a second one of the sensors, and to the porous material on a third one of the sensors;
   b) detecting responses of the sensors to the sample or environment; and
   c) employing at least one processor to determine from the responses of the sensors if the sample or environment contains one or more of the analytes.

10. The method of claim 9, wherein the processor determines respective amounts of the one or more analytes using coefficients relating the responses of the sensors to the respective masses of the analytes adsorbed or absorbed to the porous receptor materials.

11. The method of claim 9, wherein the porous receptor materials comprise metal-organic frameworks.

12. The method of claim 11, wherein each of the metal-organic frameworks has pore apertures having an average width or diameter in the range of 1 to 30 Angstroms.

13. The method of claim 9, wherein the sensor array includes at least four resonant sensors having respective resonating elements with porous receptor materials disposed thereon, and wherein the average pore size of the porous receptor materials increases systematically from the porous receptor material on the first sensor to the porous receptor material on the fourth sensor.

14. The method of claim 9, wherein the resonant sensors comprises capacitive micromachined ultrasound transducers having respective membranes, and wherein the porous receptor materials are positioned on the membranes.

15. The method of claim 9, wherein the responses of the sensors comprise frequency shifts.

16. A device comprising:
a) a sensor array comprising a plurality of resonant sensors;
b) porous receptor materials arranged on the resonant sensors, wherein the average pore size of the porous receptor materials on the sensors increases from the average pore size of a first one of the porous materials on a first one of the sensors to the average pore size of a second one of the porous materials on at least a second one of the sensors;
c) at least one detector arranged to detect responses of the sensors when the sensor array is exposed to a sample or an environment; and
d) at least one processor in communication with the detector for receiving signals or data representative of the responses of the sensors, wherein the processor is programmed to determine from the signals or data the presence, amount or relative concentration of target molecules having a size larger than the average pore size of the first one of the porous materials on the first sensor and smaller than the average pore size of the second porous material on the second sensor.

17. The device of claim 16, wherein the sensor array comprises at least N resonant sensors having respective resonating elements with the porous receptor materials disposed thereon, N is an integer greater than equal to 3, and the processor is programmed to determine the presence, amount or relative concentration of at least N–1 target molecules from the responses of the N sensors.

18. The device of claim 17, wherein the processor is programmed to determine respective amounts of the target molecules using coefficients relating the responses of the N sensors to the respective masses of the target molecules adsorbed or absorbed to the porous receptor materials.

19. The device of claim 16, wherein the porous receptor materials comprise metal-organic frameworks.

20. The device of claim 19, wherein each of the metal-organic frameworks has pore apertures having an average width or diameter in the range of 1 to 30 Angstroms.

21. The device of claim 16, wherein the sensor array includes at least four resonant sensors having respective resonating elements with the porous receptor materials disposed thereon, and wherein the average pore size of the porous receptor materials increases systematically from the porous receptor material on the first sensor to the porous receptor material on the fourth sensor.

22. The device of claim 16, wherein the resonant sensors comprises capacitive micromachined ultrasound transducers having respective membranes, and wherein the porous receptor materials are positioned on the membranes.

23. The device of claim 16, wherein the responses of the sensors comprise frequency shifts.

24. A method comprising:
a) exposing a sensor array to a sample or an environment that potentially contains one or more target molecules, the sensor array comprising a plurality of resonant sensors and porous receptor materials arranged on the resonant sensors, wherein the average pore size of the porous receptor materials on the sensors increases from the average pore size of a first one of the porous materials on a first one of the sensors to the average pore size of a second one of the porous materials on at least a second one of the sensors;
b) detecting responses of the sensors to the sample or environment; and
c) employing at least one processor to determine from the responses of the sensors the presence, amount or relative concentration of the target molecules having a size larger than the average pore size of the first one of the porous materials on the first sensor and smaller than the average pore size of the second porous material on the second sensor.

25. The method of claim 24, wherein the sensor array comprises at least N resonant sensors having respective resonating elements with the porous receptor materials disposed thereon, N is an integer greater than equal to 3, and the processor determines the presence, amount or relative concentration of at least N–1 target molecules from the responses of the N sensors.

26. The method of claim 24, wherein the processor determines respective amounts of the target molecules using coefficients relating the responses of the sensors to the respective masses of the target molecules adsorbed or absorbed to the porous receptor materials.

27. The method of claim 24, wherein the porous receptor materials comprise metal-organic frameworks.

28. The method of claim 27, wherein each of the metal-organic frameworks has pore apertures having an average width or diameter in the range of 1 to 30 Angstroms.

29. The method of claim 24, wherein the sensor array includes at least four resonant sensors having respective resonating elements with the porous receptor materials disposed thereon, and wherein the average pore size of the porous receptor materials increases systematically from the porous receptor material on the first sensor to the porous receptor material on the fourth sensor.

30. The method of claim 24, wherein the resonant sensors comprises capacitive micromachined ultrasound transducers having respective membranes, and wherein the porous receptor materials are positioned on the membranes.

31. The method of claim 24, wherein the responses of the sensors comprise frequency shifts.

* * * * *